(12) United States Patent
Hanke

(10) Patent No.: US 8,183,020 B2
(45) Date of Patent: May 22, 2012

(54) ENZYMATIC OXIDATION OF HYDROXYMETHYLFURFURAL

(75) Inventor: Paul D. Hanke, Urbana, IL (US)

(73) Assignee: Archer Daniels Midland Company, Decatur, IL (US)

( * ) Notice: Subject to any disclaimer, the term of this patent is extended or adjusted under 35 U.S.C. 154(b) by 693 days.

(21) Appl. No.: 12/222,493

(22) Filed: Aug. 11, 2008

(65) Prior Publication Data

US 2009/0053780 A1 Feb. 26, 2009

Related U.S. Application Data

(60) Provisional application No. 60/955,105, filed on Aug. 10, 2007, provisional application No. 61/047,304, filed on Apr. 23, 2008.

(51) Int. Cl.
*C12P 17/04* (2006.01)
(52) U.S. Cl. ......... 435/126; 435/132; 435/147; 435/189
(58) Field of Classification Search .................. 435/132, 435/136, 189, 126, 147
See application file for complete search history.

(56) References Cited

U.S. PATENT DOCUMENTS 7,183,421 B2 2/2007 Tanaka et al.
7,247,722 B2 7/2007 Cimedoglu et al.

FOREIGN PATENT DOCUMENTS

EP 0 356 703 7/1989

OTHER PUBLICATIONS

Enzyme Nomenclature. Edwin C. Webb, Ed. (1992) (Academic Press, Inc.: San Diego, CA), pp. v-vii.*
Isobe et al. J. Biosci. Bioengineer. (2007) 104(2): 124-128.*
Patent Cooperation Treaty, Invitation to Pay Additional Fees and Annex to Form PCT/ISA/206 Partial International Search Report issued in International Patent Application No. PCT/US2008/009598 dated on Feb. 2, 2009.
MPJ Van Deurzen et al "Chloroperoxidase-Catalyzed Oxidation of 5-Hydroxymethylfurfural" Journal of Carbohydrate Chemistry, vol. 16, No. 3 pp. 299-309 Marcel Dekker, Inc. 1997.
MPJ Van Deurzen et al "Selective Oxidations Catalyzed by Peroxidases" Tetrahedron vol. 53, No. 39 pp. 13183-13220 Elsevier Science Ltd, Amsterdam, Netherlands 1997.
Zaks et al "Chloroperoxidase-Catalyzed Asymmetric Oxidations: Substrate Specificity and Mechanistic Study" Journal of the American Chemical Society vol. 117, No. 42 Oct. 25, 1995.
Grabowski et al "Method of Obtaining 2, 5-Furanedicarboxylic Acid" Database Caplus Copyright 2009, Database accession No. 123:299957.
Mitsukura et al "Oxidation of Heterocyclic and Aromatic Aldehydes to the Corresponding Carboxylic Acids by *Acetobacter* and *Serratia* Strains" Biotechnology Letters pp. 1643-1648 Kluwer Acedemic Publishers, 2004.
International Search Report and Written Opinion of The International Searching Authority, issued in International Patent Application No. PCT/US2008/009598, mailed Apr. 9, 2009.

* cited by examiner

*Primary Examiner* — Susan Hanley
(74) *Attorney, Agent, or Firm* — Mark W. Roberts

(57) ABSTRACT

A method of converting hydroxymethylfurfural and is derivative species into hydroxymethylfurfural oxidation products is disclosed. The method includes contacting the hydroxymethylfurfural species in a mixture with an enzyme that oxidizes the hydroxymethylfurfural species while controlling hydrogen peroxide in the mixture. In one exemplary embodiment the enzyme is chloroperoxidase and the hydrogen peroxide is metered into the mixture to predominantly and selectively make at least one of formylfuran carboxylic acid or furan dicarboxylic acid. In another embodiment the enzyme is aryl alcohol oxidase and catalase is included in the mixture to remove unwanted hydrogen peroxide by product and the reaction predominantly makes at least one of dimethylfuran or formylfuran carboxylic acid. When the predominant product is a carboxylic acid or furan dicarboxylic acid, it can be recovered in substantially pure form by acid precipitation.

7 Claims, 1 Drawing Sheet

ENZYMATIC OXIDATION OF HYDROXYMETHYLFURFURAL

CROSS REFERENCE TO PROVISIONAL APPLICATION

This application is based upon and claims the benefit of priority from Provisional U.S. Patent Application 60/955,105 filed on Aug. 10, 2007, and from Provisional U.S. Patent Application 61/047,304 filed on Apr. 23, 2008, the entire contents of which are incorporated by reference herein.

TECHNICAL FIELD

This disclosure relates to a method of oxidizing hydroxymethylfurfural. More particularly, this disclosure relates to a method of catalytically oxidizing hydroxymethylfurfural with an oxidant in the presence of an enzyme to selectively form oxidation products of hydroxymethylfurfural.

INTRODUCTION

The use of natural products as starting materials for products is a growing industry. For example, a great deal of research is being conducted to convert natural products into fuels as a cleaner alternative to fossil-fuel based energy sources. Agricultural raw materials such as starch, cellulose, sucrose or inulin are inexpensive and renewable starting materials for the manufacture of hexoses, such as glucose and fructose. Glucose and other hexoses, and particularly fructose, which is an abundant compound derived from natural products such as corn, may be converted to other materials, such as hydroxymethylfurfural (HMF).

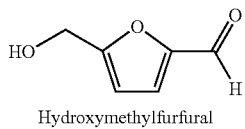

Hydroxymethylfurfural

HMF is an important compound because its derivatives have many potential uses, such as use as biofuels, in polymeric coatings and adhesives, and as biobased substitutes for oil-derived chemicals.

One potential series of useful derivatives are compounds resulting from the oxidation of HMF. A wide variety of products may be obtained through the oxidation of HMF. The most common products are hydroxymethylfurancarboxylic acid (HmFCA), formylfuran carboxylic acid (FFCA), 2,5-furandicarboxylic acid (FDCA), and diformylfuran (DFF) as shown in the diagram below:

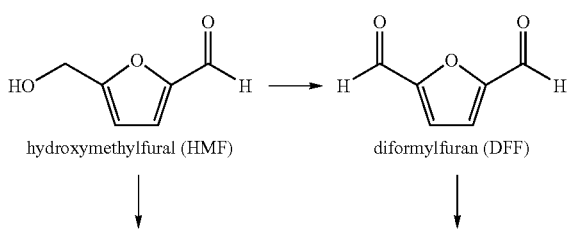

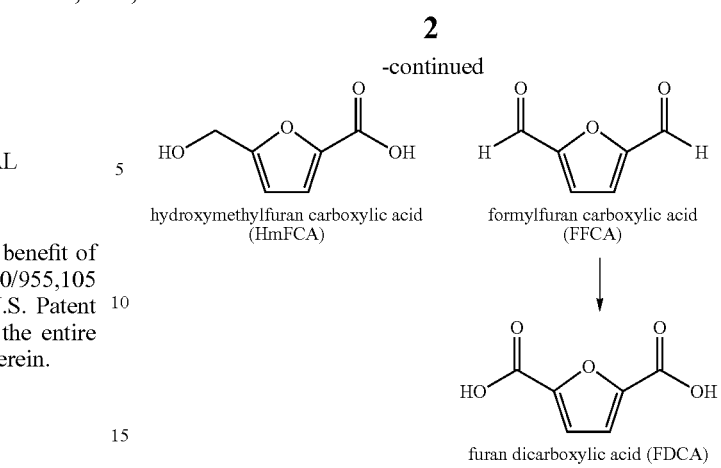

HMF oxidation products have important commercial value. For example, FDCA is a chemical that can be used as a substitute for ethylene terephthalate or butylene terephthalate in the production of polyester polymers. Derivatives made from FDCA, such as 2,5-dihydroxymethylfuran and 2,5-bis(hydroxymethyl)tetrahydrofuran, can also be used to make polyester polymers.

However, the ability to convert HMF into one specific oxidation product is often difficult in practice. This is due to the ability of the alcohol and aldehyde portions of the HMF molecule to undergo a variety of oxidation reactions. For example, Tanaka et al. (U.S. Pat. No. 7,183,421) describes a process for producing oxide from an alcohol compound via reacting the alcohol compound on a silica gel scaffold in the presence of an oxidative catalyst. The process results in aldehyde, ketone, lactone and carboxylic acid derivatives of the alcohol. However, in order to obtain one specific oxidation product, complicated and costly time-consuming steps of purification of the reaction mixture must be performed.

Cimedoglu et al. (U.S. Pat. No. 7,247,722) describes a method of preparing polysaccharide aldehydes from polysaccharides by nitroxyl radical mediated aqueous oxidation. However, this procedure results in limited conversion of the alcohol of the polysaccharide to an aldehyde, with a major side product being a carboxylic acid. Furthermore, the reaction is not selective, with from 10 to 400% mole ratio of carboxylic acid to aldehyde produced.

Enzymatic oxidation could potentially offer a fast and efficient method for oxidizing alcohols. However, the active sites of enzymes are typically specific to particular substrates or types of substrates commonly made in living organisms. HMF and its oxidized derivatives are not commonly known to be made by enzymatic action in a living organisms so it would be surprising to find an enzyme capable of oxidizing HMF to its derivatives, such as DFF, HmFCA, FFCA and FDCA at sufficiently high yields and with minimal side products to be useful.

Deurzen et al., *J. Carbohydrate Chemistry* 16(3), 299-309 (1997) described the oxidation of HMF to DFF with hydrogen peroxide using chloroperoxidase catalyst. However, this method only resulted in the production of results in 60-74% yield of DFF with a major side product of HmFCA at 25-40% yield.

SUMMARY OF THE DISCLOSURE

Figure 1:
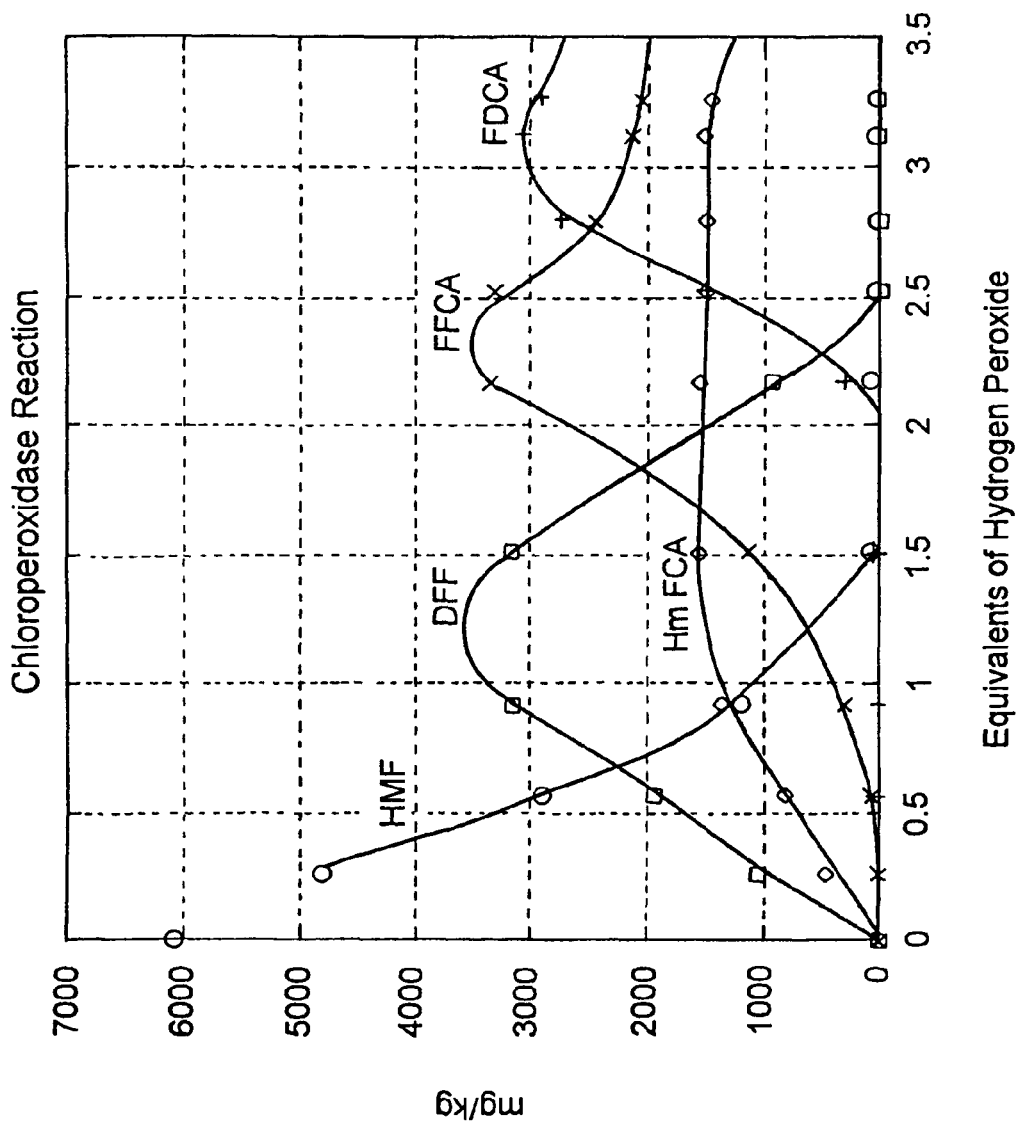
FIG. 1 graphically illustrates the amount of DFF, HmFCA, FFCA and FDCA produced in accordance with the controlled rate of addition of equivalents of hydrogen peroxide substrate to chloroperoxidase in the reaction mixture as one embodiment of the disclosure.

In order to overcome the disadvantages inherent in the prior art, this disclosure provides a method of converting HMF into HMF oxidation products. In one embodiment, the method of oxidizing substituted or unsubstituted hydroxymethylfurfural species comprises the steps of adding a hydroxymethylfurfural species to a buffered aqueous solution; adding an amount of enzyme to the solution sufficient to oxidize the hydroxymethylfurfural; adding an oxidant; and stirring the solution at room temperature for a period of time sufficient to convert substantially all of the substituted or unsubstituted hydroxymethylfurfural to an oxidized product.

In one embodiment there is described a method of oxidizing a hydroxymethylfurfural species, that includes, contacting the hydroxymethylfurfural species with a chloroperoxidase in a mixture while controlling an amount of hydrogen peroxide in the mixture over a sufficient time to oxidize a majority of the hydroxymethylfurfural species in the mixture and predominantly obtain a selected oxidized product having a carboxylic acid residue at a $C_1$ position of the hydroxymethylfurfural species. When the hydroxymethylfurfural species is hydroxymethylfurfural the selected oxidized product is predominantly one of formylfuran carboxylic acid or furan dicarboxylic acid, and in some embodiments the predominant product is furan dicarboxylic acid. In certain further embodiments the selected oxidized product is recovered in substantially pure form by precipitating the product out of the mixture by lowering the pH to precipitate the acid. The method is also demonstrated to work when he hydroxymethylfurfural species is selected from the group consisting of a hydroxymethylfurfural ether and a hydroxymethylfurfural ester at the $C_6$ position of hydroxymethylfurfural, where the predominant oxidized hydroxymethylfurfural product is a $C_1$ acid of the hydroxymethylfurfural ether or ester.

In another embodiment there is disclosed a method of oxidizing hydroxymethylfurfural that includes contacting hydroxymethylfurfural with an oxidase in the presence of an oxidizing substrate in a mixture under conditions, and for a time period sufficient to oxidize the hydroxymethylfurfural to at least one of diformylfuran or formylfuran carboxylic acid. The method may further include removing hydrogen peroxide formed in the mixture with catalase. Embodiments of the method are exemplified where the oxidase is an aryl alcohol oxidase. Typically, diformylfuran is the predominant product, but in other embodiments formylfuran carboxylic acid is the predominant product.

In one embodiment, hydroxymethylfurfural is converted into DFF comprising the steps of combining aryl-alcohol oxidase and air with hydroxymethylfurfural to form a reaction mixture followed by conversion to DFF in high yield. In another embodiment the DMF is further oxidized to FFCA as the predominant product with some aryl-alcohol oxidase. The method optimally includes the addition of catalase.

In a typical embodiment, the reaction mixture includes a buffered solution. The pH of the buffered system is in a range of about 6.0 to about 9.0. In yet another embodiment, the method further comprises the step of aerating the reaction mixture for a period of time sufficient to allow for the conversion of substantially all of the hydroxymethylfurfural into DFF.

This disclosure also provides a method of producing a furan carboxylic acid where the $C_1$ carbon of the hydroxymethylfurfural nucleus of (i.e., hydroxymethylfurfural itself or a substituted derivative thereof) is oxidized to a carboxylic acid group. The method comprises the steps of forming a mixture of an oxidizing enzyme and hydroxymethylfurfural species and adding an oxidant at a controlled rate of addition to the mixture to form the furan carboxylic acid. Typically, the rate of oxidant addition is from about 0.2 to about 1.5 substrate equivalents per hour, more typically, about 0.5 equivalents per hour.

In another method, the catalytic enzyme is chloroperoxidase, which uses hydrogen peroxide as the oxidant. Typically, the concentration of hydrogen peroxide is from between 1% to 10% by volume. More typically, the concentration of the hydrogen peroxide is 3% by volume.

The method may further include the step of precipitating the furan carboxylic acid from an aqueous solution and may include recrystallizing the precipitate to form substantially pure furan carboxylic acid.

DETAILED DESCRIPTION OF THE DISCLOSURE

In a broad aspect, the present disclosure discloses methods of selectively producing at least one of a $C_1$ or $C_6$ oxidized product of hydroxymethylfurfural and its derivative species by use of an oxidizing enzyme. As used herein a "hydroxymethylfurfural species" means hydroxymethylfurfural and substituted derivatives of hydroxymethylfurfural, having the general formula:

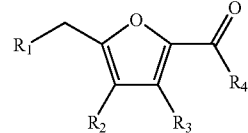

To be clear, in the structure above the aldehyde group is on the $C_1$ carbon and $R_1$ is attached to the $C_6$ carbon and the hydroxymethylfurfural species include those wherein $R_1$ is H, OH, or a $C_1$-$C_{10}$ alkyl, allyl, acyl, aryl, or RO— ether moiety, including cyclic groups; $R_2$ and $R_3$ are independently H, OH, or a $C_1$-$C_{10}$ alkyl, allyl, acyl, aryl, or ether moiety, including cyclic groups; and $R_4$ is H, OH, or a $C_1$-$C_{10}$ alkyl, allyl, acyl, aryl, or RO— ether moiety, including cyclic groups; with the proviso that $R_1$ and $R_4$ are not simultaneously acid groups at the $C_1$ and $C_6$, positions, in which case the HMF species would be fully oxidized at the $C_1$ and $C_6$ positions such as in the case of FDCA. Exemplary embodiments demonstrate the oxidation of HMF, and $C_1$ to $C_4$ HMF ethers and ester derivatives of HMF at the $C_6$ position, however these embodiments are exemplary only, as one of ordinary skill in the art would understand that the enzymatic oxidations described herein would be expected to work with a variety of HMF species.

Surprisingly, a variety oxidizing enzymes are suitable for use in different embodiments of the methods provided herein. In certain embodiments, the oxidizing enzyme is an oxidase, best exemplified herein with an aryl alcohol oxidase. As shown in the example to follow herein, routine screening may be used to identify other oxidases that oxidize HMF, and several were shown to provide this function at least to a limited extent as exemplified. It may be noted that the following oxidases did not function to oxidize hydroxymethylfurfural: Alcohol oxidase from *Candida boidinii*, Ascorbate oxidase from *Cucurbita* sp. and Laccase from *Rhus vernificera*.

In other embodiments the oxidizing enzyme is a peroxidase, exemplified herein with a chloroperoxidase. It is anticipated that other peroxidases other than chloroperoxidases should also function to oxidize hydroxymethylfurfural species and functional peroxidases can be identified by routine screening using the guidance provided herein. It may be noted that the following peroxidases did not function to oxidize HMF: bromoperoxidase from *Corallina officinalis*, Horseradish peroxidase, soybean peroxidase, lignin peroxidase, manganese peroxidase, lactoperoxidase from bovine milk, glucose oxidase from *Aspergillus niger*, galactose oxidase from *Dactylium dendroides*, and alcohol oxidase from *Pichia pastoris*.

Although use of either an oxidases or peroxidase are independent embodiments of the present disclosure, one linking feature of the use of either type of enzyme is controlling the hydrogen peroxide in the reaction mixture. In the case of oxidases, the oxidizing substrate is oxygen and hydrogen peroxide is a by-product of the oxidation. In the case of peroxidases, hydrogen peroxide is the oxidizing substrate and therefore required in the reaction mixture. A problem with hydrogen peroxide is that it is a strong and indiscriminant oxidant of proteins, hence its presence in the reaction mixture can cause inactivation of the enzymes used to oxidize the hydroxymethylfurfural species. Therefore controlling the hydrogen peroxide in the mixture is an important advantage of the present teaching.

As used herein, "controlling the hydrogen peroxide in the reaction mixture" means in the case of oxidases, the hydrogen peroxide is eliminated from the reaction mixture, or in the case of peroxidases, the hydrogen peroxide is metered into the reaction mixture. The hydrogen peroxide is eliminated from the reaction mixture with oxidases, by adding catalase, which converts hydrogen peroxide into water and oxygen, the later of which can again act as substrate for the oxidase. In the case of metering, hydrogen peroxide is slowly added to the reaction mixture containing peroxidase in controlled amounts over the reaction time period. The amount metered is expressed in equivalents of hydrogen peroxide relative to the hydroxymethylfurfural substrate. It has been discovered that by appropriate metering in this manner, the product of HMF oxidation can be selectively enriched for the desired oxidized species. This is in contrast to the teaching of Druezen, which only demonstrated predominant production of the first oxidized product, DFF at up to 74% yield with HmFCA representing the bulk of the remaining products and only minimal amounts (less than 5%) of FFCA being produced. In contrast, according to the present teaching, with metering, the reaction can be driven to selectively enrich for the production of FFCA or FDCA as the predominant product at least 30% or more typically at least 50% yield as illustrated in FIG. 1. The metering of slightly more than one equivalent of HMF over the reaction period selectively enriches for the production of DFF, however, continued metering of slightly more than two equivalents selectively enriches for FFCA, and the metering of slightly more than three equivalents selectively enriches the production of FDCA.

In one embodiment, the method comprises the steps of combining an enzyme with hydroxymethylfurfural in the presence of oxygen under aqueous conditions followed by conversion to diformylfuran. The reaction starts with hydroxymethylfurfural as the substrate to be oxidized. In another embodiment the hydroxymethylfurfural species can be can be a substituted hydroxymethylfurfural and the oxidized product is the HMF carboxylic acid.

In exemplary embodiments, aryl-alcohol oxidase is used as a catalyst for the conversion of HMF to DFF. Aryl-alcohol oxidase (AAO) allows for the selective oxidation of HMF to DFF or in some cases to FFCA as the predominant product without the formation of significant amounts of side products.

The method typically includes the addition of catalase. The source of the catalase is not important but is exemplified herein using Fermcolase™ (Danisco US Inc., Genencor Division, Rochester, N.Y.). In one embodiment, hydrogen peroxide is generated during the reaction as a result of the oxidation of the alcohol to the aldehyde. Since hydrogen peroxide reacts further with the aldehyde moiety to produce carboxylic acids and other oxidation products, it may be desirable to remove the hydrogen peroxide from the reaction mixture in order to increase the yield of DFF. Catalase converts hydrogen peroxide to water and oxygen. Typical embodiments use an amount of catalase sufficient to convert any hydrogen peroxide generated into water and oxygen and therefore minimize unwanted oxidation of the enzyme.

Furthermore, AAO utilizes oxygen as the oxidant during the reaction. The most economical source of oxygen is air. This is advantageous in that air is easily obtained from the atmosphere at no cost, no toxicity and no need to remove it after the reaction. Alternatively, one may employ a molecular oxygen liberating system. The oxygen-generating system may in principle be chosen from the various oxygen-generating systems which have been disclosed in the art. For example, one may use the catalase enzymes already present in the reaction mixture to generate oxygen from hydrogen peroxide.

In an exemplary embodiment, the reaction mixture further comprises a buffered solution, with the pH of the buffered system in a range of about 6.0 to about 9.0. More typically, the pH range is from about 6.5 to 7.5. Any buffer having a buffering range within the desired range which does not substantially inhibit the oxidation capability of the enzyme is suitable. Some buffers within this range are, but not limited to, carbonate, 1,4-piperazinediethanesulfonic acid (PIPES), 4-morpholinepropanesulfonic acid (MOPS), 4-(2-hydroxyethyl)-1-piperazineethane-sulfonic acid (HEPES), triethanolamine, TRIS, phosphate and the like.

In an exemplary practice, the method includes mixing or agitating the reaction mixture to dissolve air into the mixture for a period of time sufficient to allow for the conversion of substantially all of the HMF into DFF or FFCA. For example, the rotation period may be 24 hours or less. Typically, the period of rotation is 5 hours or less or more typically 2 hours or less.

The temperature at which the method is conducted may be any temperature which allows for the reaction to proceed substantially to completion. Generally, enzymes are able to react at temperatures ranging from 0 to 80° C. Typically, the method is conducted from about 10 to about 50° C. More typically, the method is conducted from about 15 to about 35° C. Most typically, the method is conducted from about 20 to about 30° C. or room temperature.

In other embodiments, it is desired to convert HMF into products with higher oxidation state than DFF. These products require more oxidation to take place during the course of the reaction. FIG. 1 graphically illustrates the embodiment referred to above. It shows the concentration of the reaction intermediates formed as the reaction proceeds, i.e., DFF, FFCA, FDCA and HmFCA. The rate of addition of the oxidant must be sufficient to oxidize HMF and DFF completely. Also, if the addition of the oxidant is not controlled, any excess oxidant in the reaction system may destroy the catalyst. In order to convert all of the HMF to FDCA a strong oxidant must be used. Hydrogen peroxide ($H_2O_2$) is the typical oxidant for this embodiment.

In the embodiment depicted in FIG. 1, chloroperoxidase was used as the catalyst. Chloroperoxidase (E.C. 1.11.1.10) is derived from *Caldariomyces fumago* and is a heme peroxidase, containing iron(III) protoporphyrin(IX) as the prosthetic group. It is an extracellular enzyme that can be readily isolated in synthetically useful quantities. Chloroperoxidase catalyzes a variety of oxidations with hydrogen peroxide via the formation of an oxoiron(V) porphyrin intermediate.

As illustrated in the FIG. 1, as 0.5 to 1.25 equivalents of oxidant is added, the amount of HMF decreases rapidly to form HmFCA and DFF, giving a 33% and 67% yield, respectively. When about 1.25 and 2.25 equivalents of oxidant is slowly added to the reaction mixture, the amount of HmFCA in the reaction mixture remains constant. The concentration of HmFCA does not change once the initial amount is formed indicating that it cannot be further oxidized in the presence of chloroperoxidase. As DFF is completely oxidized, the amount of FFCA increases. As the amount of oxidant added increases above 2.25 equivalents, the amount of FFCA decreases and the amount of FDCA increases substantially providing a yield of about a 50% or more. Substantially all of the DFF is ultimately converted to FFCA and FDCA. An optimal amount of FDCA formed occurs between 3 and 3.5 equivalents of oxidant added to the reaction. During the course of the reaction, there is no need to add additional enzyme catalyst to catalyze the reaction. The pH of the reaction system ranges from about pH 3 to about pH 8 and more typically from between about pH 5 to about pH 6 during the reaction.

One desirable oxidation product is FDCA. In order to produce high yields of FDCA, the amount of oxidant added to the reaction may be controlled. The oxidant is added at a slow rate of about 0.2 to about 1.5 equivalents per hour or at a rate of about 0.3 to about 1.0 equivalents per hour or at a rate of about 0.5 to about 0.8 equivalents per hour. The oxidant may be added as an aqueous solution having an oxidant concentration between 1% to 10%. The concentration must be sufficient to oxidize the HMF and each succeeding intermediate in the process. The concentration of the oxidant is inversely proportional to the rate of addition of the oxidant, i.e., the more concentrated the oxidant, the slower the rate of addition. In one embodiment, 3% $H_2O_2$ is added is added to a solution of HMF at a rate of 0.5 equivalents per hour in the presence of chloroperoxidase. The furan dicarboxylic acid product may then be precipitated by lowering the pH of the mixture to about 3 or less.

In this disclosure, when referring to the amount of oxidation product formed from HMF in these disclosed methods, the term "predominant product" and variations thereof means the desired (i.e., "selected") product represents the majority of the products in the reaction mixture, typically being at least 30% and more typically at least 50% of the product content. The phrase "substantially all" means 90% or greater conversion of HMF to an oxidation product. In some embodiments, "substantially all" means 95% or greater conversion, and more typically, "substantially all" means 98% or greater conversion. The phrase "substantially pure" means that by visual detection on a TLC plate, there is no other product visible other than the desired product. Without being restricted to actually percentages, it is believed this typically means 90% 95% or even greater purity of at least 98%. It is submitted that one skilled in the art would readily understand the meaning of the phrases "substantially all" and "substantially pure".

EXAMPLES

Example 1A

Screening Oxidases for Oxidation of HMF

Nine different Aryl-alcohol oxidases (AAO) were obtained from Biocatalytics Inc, (a.k.a Codexis Inc, Pasedena, Calif.). They were labeled AAO-101 thru AAO-109. 12.6 mg of HMF was dissolved in two ml of buffer supplied by Biocatalytics Inc. (50 mM KPO4, 10 mg/l catalase, pH 7.0—the catalase was Fermcolase™ (Danisco US Inc., Genencor Division, Rochester, N.Y.) and combined with approximately 16-20 mg of each of the nine different AAO's in a 15 ml closed tube and rotated on a tube rotator. Time points were taken at 5, 24, and 72 hr. After 72 hr all nine AAO's converted some of the HMF to DFF. AAO-109 was the worst converting only about 3% of the HMF to DFF after 72 hr. AAO-101, AAO-102, AAO-103, AAO-105, AAO-106, AAO-107, and AAO-108 made between 70% and essentially 100% DFF in 5 hr. AAO-104 was able to convert approximately 60% of the HMF to DFF in 72 hr. AAO-108 was able to further oxidize the DFF to FFCA converting about 60% of the original HMF to FFCA in 72 hr with only a small amount of FDCA (~2%). All the other AAO's were unable to convert much of the HMF to FFCA (less than 10% in 72 hr).

Alcohol Oxidase (Sigma-Aldrich, St. Louis, Mo.—item A0438) from *Hansenula* sp (22 units/mg solid) can also convert HMF to DFF. HMF (350 mg) was combined with 9 ml of water, 1 ml of 1M $KPO_4$, pH 7.5, 100 units alcohol oxidase from Hansenula, 20 ul of Fermcolase™. Samples were taken at various time points and run on TLC as in example 1. After five hours a detectable amount of DFF was seen on the TLC plates.

Pyranose Oxidase (Sigma item P4234) from *Cariolus* sp. (3.8 units/mg solid) can also convert HMF to DFF. 378 mg of HMF was combined with 9 ml of water, 1 ml of 1M $KPO_4$, pH 7.2, 20 ul of Fermcolase™ and 20 mg (~80 units) of pyranose oxidase. After 4 hr a time point was taken and run on TLC as in example 1. At four hours a detectable amount of DFF could be seen on the TLC plate.

The following p oxidases were also tested with HMF and did not oxidize HMF to DFF or any other products: Glucose oxidase from *Aspergillus niger*, Galactose oxidase from Dactylium dendroides, Alcohol oxidase from *Pichia pastoris*, Alcohol oxidase from *Candida boidinii*, Ascorbate oxidase from *Cucurbita* sp. and Laccase from *Rhus vernificera*.

Example 1B

Aryl Alcohol Oxidase Oxidation of HMF to DFF 50 mg Aryl-alcohol oxidase (Biocatalytics Inc., Cat. # AAO-101, lot # 1092403MM) was combined with 30 mg hydroxymethylfurfural in aqueous solution (Aldrich Chemical Co.), 100 µL fermcolase (Genencor), 0.5 ml 0.5 M $KHPO_4$ buffer and 4.5 mL water in a 15 mL falcon reaction tube. The reaction tube was then rotated at slow speed on a tube rotator (Barnsted/Thermolyne Labquake Model # 415110). Samples taken at 0, 2 and 24 hours were spotted on TLC plates (K5F Whatman) and developed in 85:15:2 acetonitrile:water:glacial acetic acid and visualized under UV light. Visual Analysis indicates that after 2 hours, approximately 80% of the HMF was converted to DFF. After 24 hours, substantially all of the HMF was converted to DFF.

Example 2

Aryl Alcohol Oxidase Oxidation of HMF to DFF and Other Oxidized Derivatives 12.64 mg hydroxymethylfurfural (Aldrich Chemical Co.) was combined with 16.7 mg Aryl-alcohol oxidase (Biocatalytics Inc.) and 33 µL catalase (Biocatalytics Inc.) in a 15 mL falcon tube and aerated as in Example 1. Samples were taken at 0, 5, 24 and 72 hours and analyzed by LCMS.

| Time | HMF (mg/kg) | DFF (mg/kg) | FFCA (mg/kg) | FDCA (mg/kg) |
|---|---|---|---|---|
| 5 hrs | 9.68 | 5939.23 | 39.46 | 0.10 |
| 24 hrs | 1 | 5353 | 102 | 0 |
| 72 | 0 | 3786 | 115 | 1 |

As is shown, after 5 hrs, the reaction mixture contained 9.68 mg/kg HMF (0.15%), 5940 mg/kg DFF (94.0%), 39 mg/kg FFCA (0.62%). Thus, after 5 hours, the conversion of HMF to DFF is essentially complete, even without the use of catalase. However, as the results show, the DFF is further converted to other products when no catalase is present in the reaction mixture.

Example 3

Chloroperoxidase Oxidation of HMF to DFF, FFCA and FDCA by Metering Hydrogen Peroxide Chloroperoxidase (E.C. 1.11.1.10) was obtained from Sigma Chemical Co., 5-hydroxymethylfurrural was obtained from Aldrich Chemical Co., and 30% hydrogen peroxide was obtained from Sigma Chemical Co. In a small beaker, 159 mg of HMF was dissolved in 20 mL of $H_2O$ along with 2.5 mL of 1M $KHPO_4$ buffer pH 5.0. To this solution was added 1600 units of chloroperoxidase. The hydrogen peroxide solution was 3% (18 mls $H_2O$ and 2 mls 30% w/w hydrogen peroxide). The solution of hydrogen peroxide was metered into a stirred HMF solution with a piston pump at a rate of 0.7 mL/hr. Time points are taken at various times after the start of the reaction. After the reaction was completed, the pH was adjusting to about 3 to cause a precipitate to form, which is substantially pure FDCA. This precipitate was spun down in a centrifuge and re-suspended in water. The pH was adjusted again to about 3 and the FDCA was crystallized again. Substantially pure FDCA is recovered. The yield of FDCA in the reaction was 65%.

Example 4

Metering for Chloroperoxidase Oxidation of DFF to FDCA Enriched Product

Chloroperoxidase (E.C. 1.11.1.10) was obtained from Sigma Chemical Co(C0278)., 5-hydroxymethylfurrural was obtained from Aldrich Chemical Co., and 30% hydrogen peroxide was obtained from Sigma Chemical Co. In a small beaker, 159 mg of HMF was dissolved in 20 mL of $H_2O$ along with 2.5 mL of 1M $KHPO_4$ buffer pH 5.0. To this solution was added 1600 units (44 ul) of chloroperoxidase. The hydrogen peroxide solution was ~3% (18 mls $H_2O$ and 2 mls 30% w/w hydrogen peroxide). The solution of hydrogen peroxide was metered into a stirred HMF solution with a piston pump at a rate of 0.7 mL/hr. Time points are taken at various times after the start of the reaction.

In a small beaker 80 mg of DFF was dissolved in 11 ml of water along with 1.25 mL of 0.8 M Na Citrate buffer pH 5.0. To this solution was added 800 units of chloroperoxidase (35 µl). A solution of 3% hydrogen peroxide was metered into the stirred DFF solution with a piston pump at a rate of 0.7 mL/hr. Various time points were taken and run on TLC as described in example 1. From the DFF both FFCA and FDCA are formed as seen on the TLC plate.

Example 5

Metering for Chloroperoxidase Oxidation of FFCA to FDCA Enriched Product

In a small beaker 80 mg of FFCA is dissolved in 10 mL of water along with 1.25 mL of 1M $KHPO_4$ buffer pH 5.0. To this solution is added 800 units of chloroperoxidase. A solution of 3% hydrogen peroxide is metered into the stirred FFCA solution with a piston pump at a rate of 0.7 mL/hr. After the addition of approximately 1 molar equivalents of hydrogen peroxide the major product, FDCA, is formed.

Example 6

Chloroperoxidase Oxidation of ethoxymethyl furfural ether to ethoxymethyl-2-furan carboxylic acid In a small beaker 80 mg of ethoxymethyl furfural is dissolved in 10 mL of water along with 1.25 mL of 1M $KHPO_4$ buffer pH 5.0. To this solution is added 800 units of chloroperoxidase. A solution of 3% hydrogen peroxide is metered into the stirred ethoxymethyl furfural solution with a piston pump at a rate of 0.7 mL/hr. After the addition of approximately 1 molar equivalents of hydrogen peroxide the major product, ethoxymethyl-2-furan carboxylic acid, is formed.

Example 7

Chloroperoxidase Oxidation of Butoxymethyl furfural ether to ethoxymethyl-2-furan carboxylic acid In a small beaker 160 mg of butoxymethyl furfural is dissolved in 11 mL of water along with 1.25 mL of 0.8M Na Citrate buffer pH 5.0. To this solution is added 800 units (35 µl) of chloroperoxidase. A solution of 3% hydrogen peroxide is metered into the stirred butoxymethyl furfural solution with a piston pump at a rate of 0.7 mL/hr. Various time points were taken and run on TLC as described in example 1. The TLC results show that butoxymethyl-2-furan carboxylic acid, was formed.

Example 8

Chloroperoxidase Oxidation of acetylmethyl furfural ester to ethoxymethyl-2-furan carboxylic acid In a small beaker 90 mg of acetylmethyl furfural was dissolved in 11 mL of water along with 1.25 mL of 0.8M Na Citrate buffer pH 5.0. To this solution was added 800 units (35 µl) of chloroperoxidase. A solution of 3% hydrogen peroxide was metered into the stirred acetylmethyl furfural solution with a piston pump at a rate of 0.7 mL/hr. Various time points were taken and run on TLC as described in example 1. The TLC results show that acetymethyl-2-furan carboxylic acid, is formed.

Example 9

Recovery of FDCA of Substantial Purity by Acid Precipitation

Chloroperoxidase (E.C. 1.11.1.10) was obtained from Sigma Chemical Co(C0278), 5-hydroxymethylfurrural was obtained from Aldrich Chemical Co., and 30% hydrogen peroxide was obtained from Sigma Chemical Co. In a small beaker, 157.5 mg of HMF was dissolved in 25 mL of $H_2O$ along with 2.5 mL of 1M $KHPO_4$ buffer pH 7.2. To this solution was added 1000 units (118 µl) of chloroperoxidase. The hydrogen peroxide solution was ~3% (18 mls $H_2O$ and 2 mls 30% w/w hydrogen peroxide). The solution of hydrogen peroxide was metered into a stirred HMF solution with a piston pump at a rate of 0.7 mL/hr. After 4 hr the reaction was stopped. The HPLC results showed there was about 2 g/kg FDCA in the reaction. Since there was about 20 ml of the reaction remaining this means there was approximately 40 mg of FDCA in the solution. After the reaction was completed, the pH was adjusting to about 3 to which caused a precipitate to form, which was mostly FDCA with only a little HmFCA and FFCA as visualized on TLC. This precipitate was spun down in a centrifuge and re-suspended in water. The pH was adjusted again to about 3 and the FDCA was allowed to precipitate again for approximately two days in the refrigerator. The precipitate was spun down and dried. About 15 mg of the FDCA was recovered. By TLC only an FDCA spot was visible with no HmFCA or FFCA visible. Substantially pure FDCA is recovered.

The foregoing is offered primarily for illustrative purposes. The present disclosure is not limited to the above described embodiments, and various variations and modifications may be possible without departing from the scope of the present invention.

What is claimed is:

1. A method of oxidizing hydroxymethylfurfural comprising contacting hydroxymethylfurfural with an oxidase that will oxidize hydroxymethylfurfural in the presence of oxygen in a mixture under conditions, and for a time period sufficient to oxidize the hydroxymethylfurfural to at least one of diformylfuran or formylfuran carboxylic acid, wherein the oxidase is selected from the group consisting of an aryl alcohol oxidase, an alcohol oxidase from *Hansenula* sp. and a pyranose oxidase from *Cariolus* sp.

2. The method of claim 1, further including removing hydrogen peroxide formed in the mixture while contacting the hydroxymethylfurfural species.

3. The method of claim 1, wherein the oxidase is an aryl alcohol oxidase.

4. The method of claim 1, further including simultaneously contacting the mixture with a catalase.

5. The method of claim 1, wherein the oxidase is an aryl alcohol oxidase, and further including simultaneously contacting the mixture with a catalase.

6. The method of claim 1, wherein the oxidase is an aryl alcohol oxidase and diformylfuran is the predominant product.

7. The method of claim 1, wherein the oxidase is aryl alcohol oxidase AAO-108 and the condition of time of contact is sufficient to form formylfuran carboxylic acid as the predominant product.

* * * * *